United States Patent
Bub

(10) Patent No.: US 6,664,419 B1
(45) Date of Patent: Dec. 16, 2003

(54) METHOD AND DEVICE FOR PURIFYING SUBSTANCES BY MEANS OF CRYSTALLIZATION

(75) Inventor: Guenther Bub, Marl (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 09/890,790

(22) PCT Filed: Jan. 21, 2000

(86) PCT No.: PCT/EP00/00441

§ 371 (c)(1), (2), (4) Date: Sep. 6, 2001

(87) PCT Pub. No.: WO00/45928

PCT Pub. Date: Aug. 10, 2000

(30) Foreign Application Priority Data

Feb. 5, 1999 (DE) ......................................... 199 04 820

(51) Int. Cl.⁷ ............................................... C07C 51/42
(52) U.S. Cl. ..................................................... 562/600
(58) Field of Search ........................ 562/600; 23/295 R, 23/296, 300; 62/532

(56) References Cited

U.S. PATENT DOCUMENTS

| | | | | |
|---|---|---|---|---|
| 3,403,029 A | * | 9/1968 | Malick ........................... | 99/31 |
| 4,230,888 A | * | 10/1980 | Paspek et al. ............... | 562/600 |
| 4,493,719 A | * | 1/1985 | Wintermantel et al. ....... | 62/532 |
| 4,822,585 A | * | 4/1989 | Dawless ..................... | 423/348 |
| 4,914,231 A | | 4/1990 | Manami et al. ............. | 562/429 |
| 5,344,969 A | * | 9/1994 | Iwane et al. ................. | 562/486 |
| 6,380,427 B1 | * | 4/2002 | Miyazaki et al. ........... | 562/600 |

FOREIGN PATENT DOCUMENTS

| | | |
|---|---|---|
| DE | 196 27 679 | 1/1998 |
| EP | 0 002 612 | 6/1979 |
| EP | 0 551 596 | 7/1993 |
| EP | 0 616 998 | 9/1994 |

OTHER PUBLICATIONS

Kirk–Othmer Encyclopedia of Chemical Technology 2$^{nd}$ ed., vol. 6, pp. 482–515, John Wiley & Sons, Inc. (1965).*
The Organic Chem Lab Survival Manual 4$^{th}$ ed., pp. 102–138, James W. Zubrick, John Wiley & Sons, Inc. (1997).*

* cited by examiner

Primary Examiner—Mukund J. Shah
Assistant Examiner—Zachary C. Tucker
(74) Attorney, Agent, or Firm—Oblon, Spivak, McClelland, Maier & Neustadt, P.C.

(57) ABSTRACT

The invention relates to a method and a device for purifying mixtures of substances by means of optionally fractional crystallization. During the crystallization process, impurities can precipitate in addition to the desired product, since these are present in such high concentrations that the limit of solubility is exceeded. According to the inventive method, a solvent or a mixture of solvents with a strong affinity to an impurity with a tendency to precipitate is added to the mixture of substances or the melt to be purified so that the corresponding impurity is kept in solution. If there are several impurities with a tendency to precipitate, some of the impurities can be kept in solution by adding a suitable solvent and the remainder can be separated by mechanical means, e.g. filtering by suction, centrifugation, etc.

20 Claims, 3 Drawing Sheets ively, the solid maleic acid may block pipes and valves.
METHOD AND DEVICE FOR PURIFYING SUBSTANCES BY MEANS OF CRYSTALLIZATION This application was filed under 35 U.S.C. 371, and is the national stage of PCT/EP00/00441, filed Jan. 21, 2000.

The present invention relates to a process and a device for the purification of crystallizable compounds by means of optionally fractional crystallization, wherein a molten material or a mixture containing essentially one desired compound and at least one impurity is subjected to at least partial crystallization.

At present, chemical starting materials and intermediates, particularly starting materials used in polymer production, are produced in enormous quantities. In order to meet the increasing demands with respect to quality, impurities in these products must be virtually absent.

In addition to distillation, crystallization has increasingly been used as a method of purification in recent years. The latter method is advantageous in that impurities which cannot be removed by distillation may frequently be removed by means of crystallization.

However, crystallization involves the drawback that impurities possibly present in the molten material will also precipitate during crystallization. It is a well-known fact that the desired product is depleted in the mother liquor or molten material during crystallization, and that impurities accumulate accordingly. Thus, some of the impurities reach and exceed their solubility limit in the course of the purification process. The impurities will precipitate as soon as the solubility limit is reached. These undesirable crystals then undergo sedimentation on the bottom or the walls of a crystallizer. As these crystals adhere to the surfaces, they will remain in the crystallizer when discharging the non-crystallized molten material. Then, when melting the deposited layer of crystals, where normally two or more fractions are formed, the precipitated impurities still present on the bottom and the walls of the crystallizer will be reabsorbed by the heated molten material. As a consequence, the impurities can never be removed completely and concentrate in the crystallizer.

If the desired compound is purified at least partially in a static crystallizer, the impurities will also be incorporated in the crystallized material because there is no agitation in the molten material.

For example, problems of the above-mentioned type occur in the purification of acrylic acid. Depending on the production process and the efficiency of the subsequent distillation, the prepurified acrylic acid will contain a more or less large proportion of maleic acid and phenothiazine (PTZ) which are by-products in the production of acrylic acid. According to a purification process suggested in EP-A-0,616,998, acrylic acid is purified using a combination of dynamic and static crystallization, wherein the residue from the dynamic crystallization is purified using static crystallization, and the purified acrylic acid is refed into the dynamic crystallization. As a result, the molten acrylic acid material which is refed into the static crystallizer already contains a high percentage of by-products such as maleic acid and phenothiazine (PTZ). When cooling the molten material, maleic acid and phenothiazine (PTZ) are precipitated and part thereof will subsequently be incorporated in the deposited layer of crystals.

Thus, in an industrial purification plant, several hundred kilograms of maleic acid may be formed during one day. Obviously, the solid maleic acid may block pipes and valves. Also, this maleic acid may precipitate as a solid deposit on the crystallizer walls or the bottom thereof. Therefore, it was found necessary to remove these precipitates.

Various solutions have been suggested to separate the precipitated by-products from the molten material. One solution suggests removal of the precipitated impurities by filtration. For this purpose, a static crystallizer 11 is connected with a separator 13 as illustrated in FIG. 1. Normally, the separator 13 can be a filter, but also, a centrifuging device, a suction filter, or any other device allowing separation of solid and liquid materials. The separator 13 is connected with the crystallizer 11 via pipes 15, 17. The pipe 17 is connected to tubes 19, 21 arranged on opposite sides in the bottom area of crystallizer 11. The tubes 19, 21 have a number of openings 23 preferably oriented at an angle to the crystallizer bottom. A collector channel 25 is provided in the center of the bottom 24 which is designed in a V-shaped cross-section. The collector channel is connected with separator 13 via pipe 15. Pipe 15 is provided with a pump 27 which is used to circulate the molten material.

The removal of impurities precipitating during the crystallization process is effected in such a way that molten material is withdrawn through pipe 15 by means of pump 27 and conveyed through separator 13 wherein the solids are retained. The molten material discharging from separator 13 is then refed into crystallizer 11 via pipe 17. Preferably, the flow rate of the molten material discharging from the openings 23 is selected in such a way that a laminar flow will form within the area of crystallizer bottom 24. In this way, the circulation of molten material will not interfere with the crystallization process. By continuously withdrawing the bottom layers of the molten material, it is possible to remove the gradually depositing impurities. Obviously, such a separator can be combined with any type of crystallizer where the product is deposited on cooled surfaces (e.g., falling film or static crystallizers). However, incorporation of precipitating impurities in the crystals cannot be completely avoided when using the separator as described. Also, it was found that not only maleic acid but also other compounds may undergo precipitation.

It is therefore the object of the present invention to provide a process and a device by means of which the problems mentioned above can largely be avoided. In particular, said process and device should allow for efficient purification of products where purification using fractional crystallization is impeded or made impossible due to precipitating impurities, and for further reduction of the percentage of residual impurities. Another object is to provide an improved process and a device for the purification of acrylic acid.

According to the invention, this is done by using a process wherein in case at least one impurity is present, which undergoes precipitation during the purification process as a result of surpassing the solubility limit, the molten material or the mixture to be purified is added with a solvent or a mixture of solvents in such an amount that the respective impurity is retained in solution.

The solvent or the mixture of solvents preferably has a high affinity to at least one of the impurities, i.e., the solvent preferably has a superior dissolving capacity for the impurity compared to the product to be purified. This is advantageous in that only a small amount of solvent has to be added to the molten material in order to prevent precipitation of the impurities. Moreover, only a small amount of product to be purified will dissolve in the solvent in this case, so that the efficiency of the process is maintained.

Conveniently, the suitable solvent or mixture of solvents is selected according to the well-known solubilities of these substances in the respective solvents. As is well-known, polar compounds have particularly good solubility in polar solvents and apolar substances in apolar solvents, for example. In order to increase the solubility of specific impurities, it is particularly preferred to add a solvent to the molten material, which is already present as an impurity in the employed material.

The inventive advancement of the well-known crystallization processes may be used in the purification of any material during which precipitation of impurities occurs. Fractional crystallization is preferably used as crystallization method. In particular, materials to be purified using fractional crystallization are acrylic acid, methacrylic acid, waste water, methylenediphenylisocyanate (MDI), toluenedi-isocyanate (TDI), caprolactam, benzoic acid, bisphenol A, nitrochlorobenzene, straight-chain and branched fatty acids, hydrazine, phenols such as para-, meta- and ortho-cresol, 2,6- and 3,5-dimethylphenol, naphthol and o,o-diophenol, chlorinated hydrocarbons such as dichlorobenzene and nitrochlorobenzene, naphthalene, 1-,2-methylnaphthalene, acenaphthene, fluorene, phenanthrene, adipic dinitrile, hexamethylenediamine, as well as paraffins from $C_{17}$ on.

In particular, the process according to the invention is suitable in the purification of acrylic acid by removing maleic acid and/or its anhydride and other impurities, if necessary.

The present invention is also directed to a crystallization device and plant which differs from well-known devices in that the device is provided with a connecting piece for metering a solvent or a mixture of solvents. The solvent preferably is added to a holding tank or a tank for intermediate storage of the fractions obtained. It is also preferred to add the solvent directly to the crystallizer.

BRIEF DESCRIPTION OF THE DRAWINGS

With reference to the Figures, the embodiments of the invention will be described below. The illustrations are merely by way of example and thus, do not limit the general idea of the invention.

FIG. 2 shows the crystallizer 70 according to the invention. This crystallizer 70 is a crystallizer according to FIG. 1 which, however, has an additional connecting piece 49 which can be used to meter a solvent into the crystallizer. Those skilled in the art will appreciate that this crystallizer could be any crystallizer.

Figure 3:
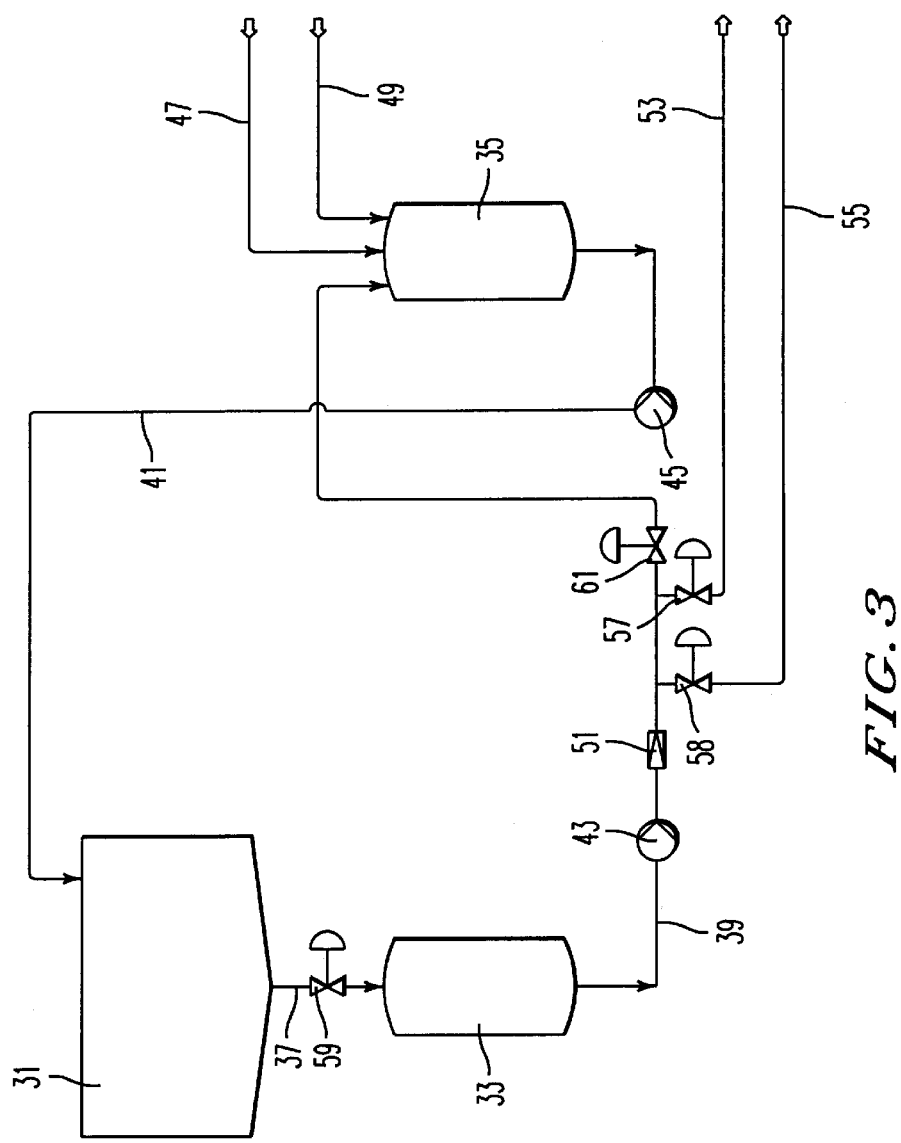
FIG. 3 likewise in schematic view, shows a crystallization plant according to the invention.

The crystallization plant schematically depicted in FIG. 3 essentially consists of a crystallizer 31 of a well-known type not specified in detail, a measuring tank 33 arranged downstream with respect to crystallizer 31, and a so-called discontinuous tank 35 wherein the employed material is put to intermediate storage. The crystallizer 31, measuring tank 33 and discontinuous tank 35 are connected via pipes 37, 39, 41. Conveying pumps 43, 45 are used to carry the molten material from measuring tank 33 to the discontinuous tank 35 and from the latter to the crystallizer 31, respectively.

A special feature of this crystallization plant is that the tank 35, in addition to a connecting piece 47 for supplying the employed material, is provided with another connecting piece 49 for supplying a solvent or a mixture of solvents. A metering device not depicted in detail allows metering an amount of solvent which corresponds to the percentage of impurities, so that precipitation of the impurities can be prevented.

Precipitations occurring in spite of the above may be filtered off by means of a filter 51 provided in pipe 39.

Those skilled in the art will appreciate that the metering of solvent can be performed automatically. For example, as soon as crystals of a specific composition accumulate in filter 51, the metering of solvent will be increased.

Two separate pipes 53, 55 connected to pipe 39 permit withdrawal of purified product or remaining residue via shut-off valves 57, 58. Further shut-off valves 59, 61 are provided between crystallizer 31 and measuring tank 33, and between measuring tank 33 and tank 35, respectively.

Figure 1:
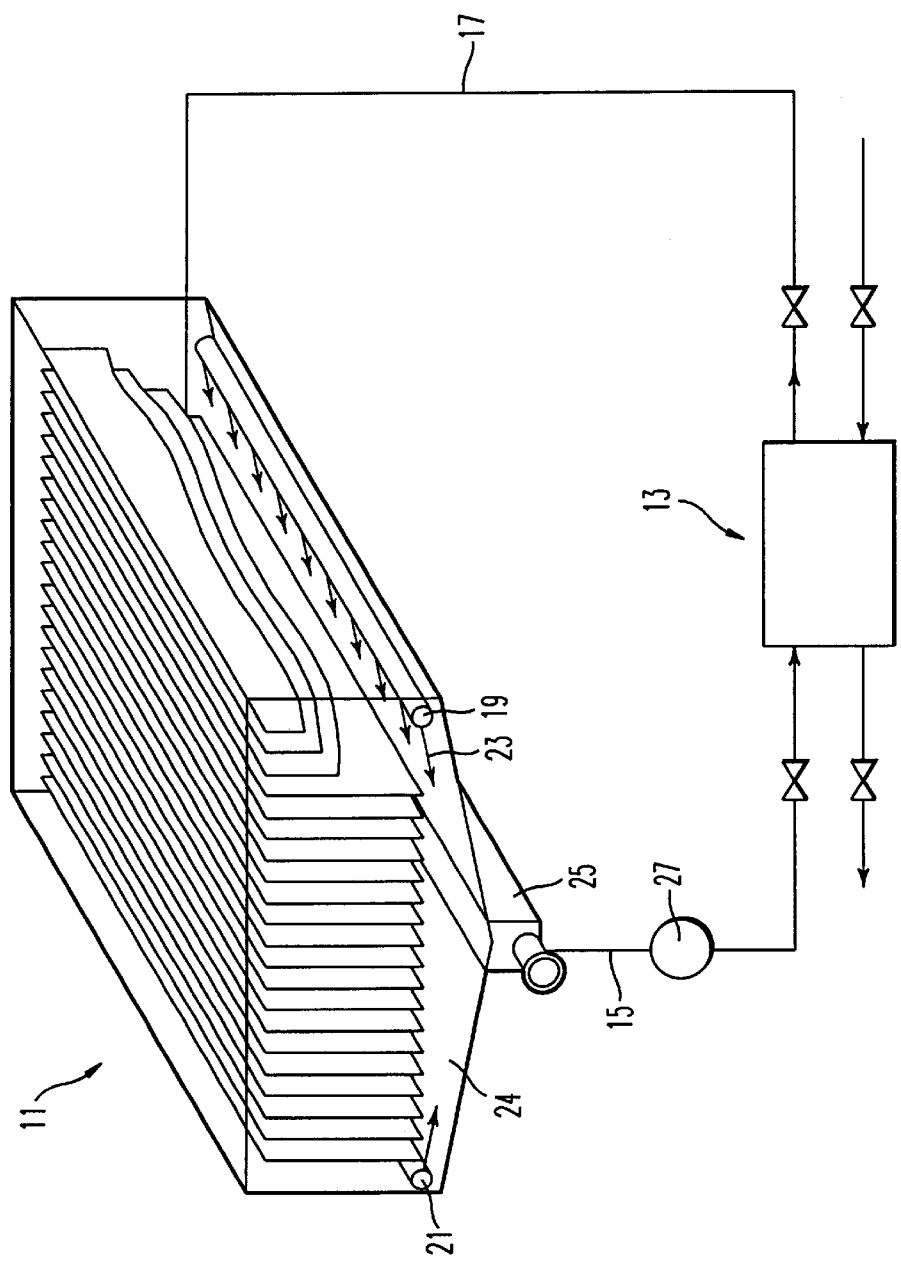
FIG. 1 shows a schematic view of a static crystallizer having a separator.
Figure 2:
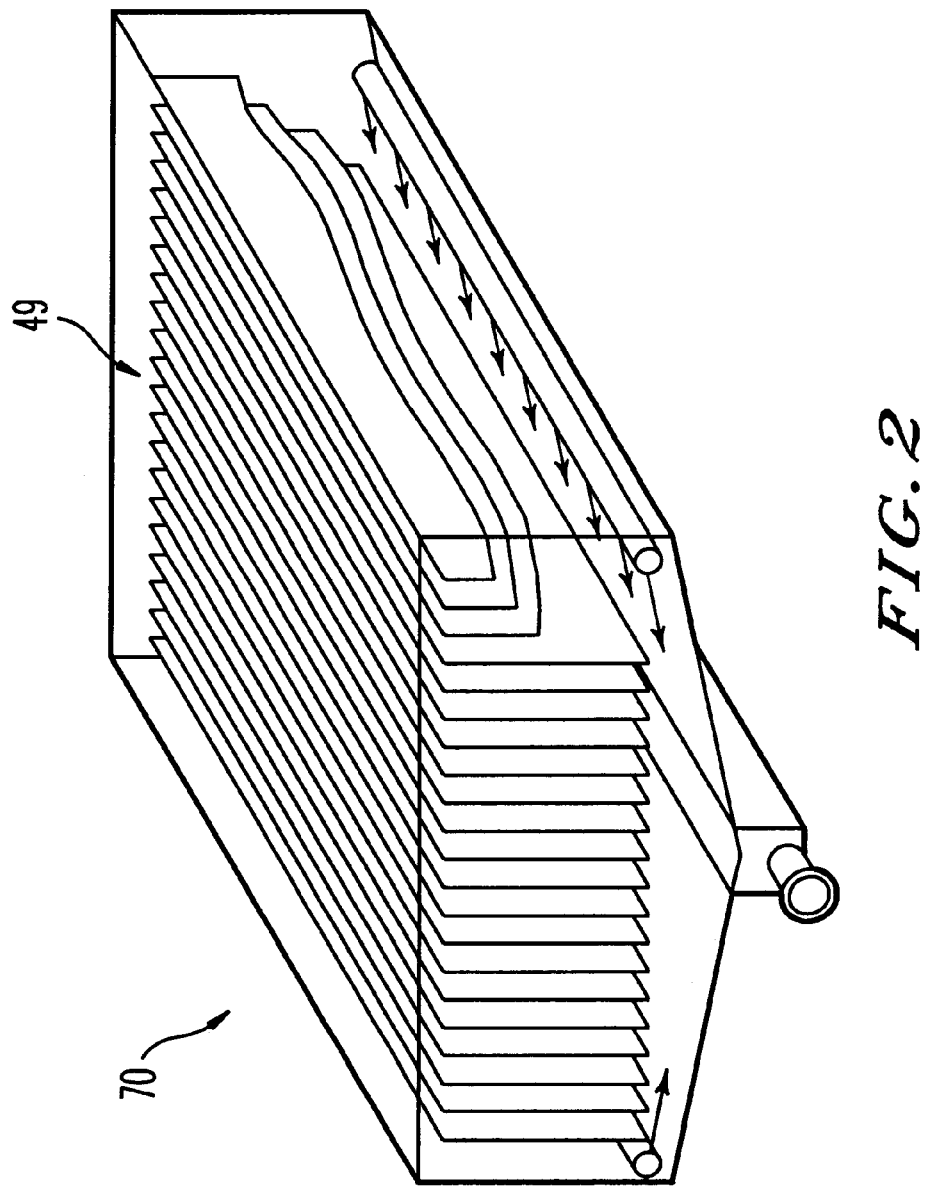
FIG. 2 shows a schematic view of a crystallizer according to the invention.

It will be understood that the plant which is depicted merely schematically in FIG. 2 may actually have multiple tanks and crystallizers. Exemplary plants have been disclosed in EP-A-0,616,998, the subject matter of which is hereby incorporated by reference and thus, is considered as part of the disclosure.

Using the example of acrylic acid purification, the process of the invention will be illustrated in more detail below.

In addition to other impurities, acrylic acid pre-purified by distillation may contain maleic acid, its anhydride, and phenothiazine which precipitate from the molten material at concentrations of more than 4% (maleic acid) and 1.5% (phenothiazine), respectively. The respective amounts of solid precipitating during a crystallization process as a result of surpassing the solubility limit can be inferred from the following Examples (Table 1 and 2).

The first line in Tables 1, 2 and 3 shows the respective composition of the employed material, the second line shows the composition of purified acrylic acid (using static crystallization) which then can be purified further by falling film crystallization, and the third line illustrates the composition of the residue obtained.

As can be seen from Table 2, 17.3 kg of residue (=mother liquor) is obtained, 3.6% (=0.62 kg) of which is PTZ. However, since the solubility of PTZ is only about 1.5%, 0.4 kg of PTZ is obtained as a solid.

As can be seen from Table 1, the case is similar with maleic acid and its anhydride, the figures in Table 1 referring to maleic acid and its anhydride, given as maleic acid. The solubility of maleic acid in acrylic acid is about 4%. The residue (13.2 kg) contains 20.4% or 2.7 kg of maleic acid, 2.4 kg of which precipitates as a solid as a result of surpassing the solubility limit.

If the employed material, which contains a total of 15% impurities (cf., Tables 1 and 2), is added with a solvent having good dissolving capacity for maleic acid and its anhydride, it is possible to retain all of the maleic acid in solution, i.e., precipitations do no longer occur.

Since maleic acid and its anhydride are known to have high solubility in water, it is possible to prevent precipitation of maleic acid by adding water to the molten acrylic acid, although the former will accumulate in the mother liquor during the crystallization process. In the Example as illustrated (Table 3), addition of 6.8 kg of water is required to keep the maleic acid dissolved in the residue. The addition of water is advantageous in that water is already present as an impurity in raw acrylic acid, i.e., no further impurity is introduced when adding water.

Because phenothiazine dissolves in water only in small amounts (dissimilar polarities), addition of water does not have a substantial impact on the solubility of phenothiazine, i.e., where an amount of more than 1.5% phenothiazine is simultaneously present in the mother liquor, precipitation of phenothiazine will continue to occur.

According to an advantageous first embodiment of the process of the invention, the suggestion is made to add a mixture of water and a low molecular weight alcohol (methanol, ethanol, n- or i-propanol) in order to retain both maleic acid and phenothiazine in solution. In principle, any other mixture of solvents can be used that achieves an increase of the solubility limits for both substances which tend to precipitate.

Because the addition of solvent requires further cooling of the molten material, a more unfavorable energy balance of the process results. Therefore, efforts are made to keep the addition of solvent as low as possible.

Alternatively, a combined process is suggested, namely, to remove the phenothiazine which, compared to maleic acid, is obtained in substantially smaller amounts, and retain maleic acid and its anhydride in solution by addition of water. As a result of combining these two methods, it is possible to achieve optimum performance of the process with respect to the energy balance.

| Reference numerals | |
|---|---|
| 11 | Static crystallizer |
| 13 | Separator |
| 15, 17 | Pipes |
| 19, 21 | Tubes |
| 23 | Tube openings |
| 25 | Collector channel |
| 31 | Crystallizer |
| 33 | Measuring tank |
| 35 | Discontinuous tank |
| 37, 39, 41 | Pipes |
| 43, 45 | Conveying pumps |
| 47 | Tank connecting piece for employed material |
| 49 | Tank connecting piece for solvent |
| 51 | Filter |
| 53, 55 | Pipes |
| 57, 58 | Shut-off valves for pipes 53, 55 |
| 59, 61 | Shut-off valves |
| 70 | Crystallizer according to the invention |

TABLE 1

Accumulation of maleic acid in the residue during acrylic acid purification (with no solvent added)

| Amount [kg] | Weight | Maleic ac. [%] | Acrylic ac. [%] | Other impurities [%] |
|---|---|---|---|---|
| Employed material | 100 | 4.0 | 85.0 | 11.0 |
| Purified fraction | 86.8 | 1.5 | 88.4 | 10.1 |
| Residue | 13.2 | 20.4 | 62.7 | 16.8 |

TABLE 2

Accumulation of phenothiazine in the residue during acrylic acid purification (with no solvent added)

| Amount [kg] | Weight | Phenothiazine [%] | Acrylic ac. [%] | Other impurities [%] |
|---|---|---|---|---|
| Employed material | 100 | 1.4 | 85.0 | 13.6 |
| Purified fraction | 82.7 | 0.9 | 89.6 | 9.4 |
| Residue | 17.3 | 3.6 | 62.8 | 33.6 |

TABLE 3

Accumulation of dissolved maleic acid in the residue during acrylic acid purification (with addition of solvent)

| Amount [kg] | Weight | Maleic ac. [%] | Acrylic ac. [%] | Other impurities [%] | Solvent [%] |
|---|---|---|---|---|---|
| Employed material | 106.8 | 3.7 | 79.6 | 10.3 | 6.4 |
| Purified fraction | 87.6 | 1.3 | 86.8 | 9.8 | 2.1 |
| Residue | 19.2 | 15.1 | 46.5 | 12.5 | 25.9 |

What is claimed is:

1. A process for the purification of acrylic acid comprising:
    crystallizing a molten material or a mixture comprising acrylic acid and at least one impurity having a tendency to precipitate;
    adding solvent or a solvent mixture to the molten material or the mixture in a quantity sufficient to retain at least one impurity having a tendency to precipitate in solution, wherein the solvent has a superior dissolving capacity for at least one of the impurities having a tendency to precipitate, compared to acrylic acid and wherein the mixture comprises two or more impurities having a tendency to precipitate selected from the group consisting of maleic acid, an anhydride of maleic acid, and phenothiazine, a quantitatively more significant impurity having a tendency to precipitate is retained in solution and wherein a solvent or a mixture of solvents is added which is suitable for retaining multiple impurities in solution; and
    removing the impurity having a tendency to precipitate, which is retained in solution, from the crystal.

2. The process according to claim 1, wherein the acrylic acid is purified by means of fractional crystallization.

3. The process according to claim 1, wherein the crystallized product formed, which comprises the desired compound in a purified form, is melted and the molten material is collected.

4. The process according to claim 3, wherein the molten material is collected in fractions.

5. The process according to claim 4, wherein the fractions obtained are subjected to at least one or more further crystallization and/or melt cycles.

6. The process according to claim 1, wherein said removing comprises employing at least one separator.

7. The process according to claim 6, wherein the separator is a filter, a suction filter or a centrifuge.

8. The process according to claim 1, wherein said solvent mixture is a water and alcohol mixture.

9. A process for the purification of acrylic acid comprising:

crystallizing a molten material comprising acrylic acid and at least one impurity having a tendency to precipitate;

adding solvent or a solvent mixture to the molten material in a quantity sufficient to retain at least one impurity having a tendency to precipitate in solution, wherein the solvent has a superior dissolving capacity for at least one of the impurities having a tendency to precipitate, compared to acrylic acid and wherein the mixture comprises two or more impurities having a tendency to precipitate selected from the group consisting of maleic acid, an anhydride of maleic acid, and phenothiazine, a quantitatively more significant impurity having a tendency to precipitate is retained in solution and wherein a solvent or a mixture of solvents is added which is suitable for retaining multiple impurities in solution; and removing the impurity having a tendency to precipitate, which is retained in solution, from the crystal.

10. A process for the purification of acrylic acid comprising:

crystallizing a molten material comprising acrylic acid and at least one impurity having a tendency to precipitate;

adding water to the molten material in a quantity sufficient to retain at least one impurity having a tendency to precipitate in solution, and wherein the mixture comprises two or more impurities having a tendency to precipitate selected from the group consisting of maleic acid, an anhydride of maleic acid, and phenothiazine, a quantitatively more significant impurity having a tendency to precipitate is retained in solution; and removing the impurity having a tendency to precipitate, which is retained in solution, from the crystal.

11. A process for the purification of acrylic acid comprising:

crystallizing a molten material or a mixture comprising acrylic acid and at least one impurity having a tendency to precipitate;

adding solvent or a solvent mixture to the molten material or the mixture in a quantity sufficient to retain at least one impurity having a tendency to precipitate in solution, wherein the solvent has a superior dissolving capacity for at least one of the impurities having a tendency to precipitate, compared to acrylic acid and wherein the mixture comprises two or more impurities having a tendency to precipitate selected from the group consisting of maleic acid, an anhydride of maleic acid, and phenothiazine, a quantitatively more significant impurity having a tendency to precipitate is retained in solution and wherein a solvent or a mixture of solvents is added which is suitable for retaining multiple impurities in solution; and removing any residual impurities still precipitating, despite the addition of said solvent or mixture of solvent, from the molten material.

12. The process according to claim 11, wherein the acrylic acid is purified by means of fractional crystallization.

13. The process according to claim 11, wherein the crystallized product formed, which comprises the acrylic acid in a purified form, is melted and the molten material is collected.

14. The process according to claim 13, wherein the molten material is collected in fractions.

15. The process according to claim 14, wherein the fractions obtained are subjected to at least one or more further crystallization and/or melt cycles.

16. The process according to claim 11, wherein said removing comprises employing at least one separator.

17. The process according to claim 16, wherein the separator is a filter, a suction filter or a centrifuge.

18. The process according to claim 17, wherein said solvent mixture is a water and alcohol mixture.

19. A process for the purification of acrylic acid comprising:

crystallizing a molten material comprising acrylic acid and at least one impurity having a tendency to precipitate;

adding solvent or a solvent mixture to the molten material in a quantity sufficient to retain at least one impurity having a tendency to precipitate in solution, wherein the solvent has a superior dissolving capacity for at least one of the impurities having a tendency to precipitate, compared to acrylic acid and wherein the mixture comprises two or more impurities having a tendency to precipitate selected from the group consisting of maleic acid, an anhydride of maleic acid, and phenothiazine, a quantitatively more significant impurity having a tendency to precipitate is retained in solution and wherein a solvent or a mixture of solvents is added which is suitable for retaining multiple impurities in solution; and removing any residual impurities still precipitating, despite the addition of said solvent or mixture of solvent, from the molten material.

20. A process for the purification of acrylic acid comprising:

crystallizing a molten material comprising acrylic acid and at least one impurity having a tendency to precipitate;

adding water to the molten material in a quantity sufficient to retain at least one impurity having a tendency to precipitate in solution, and wherein the mixture comprises two or more impurities having a tendency to precipitate selected from the group consisting of maleic acid, an anhydride of maleic acid, and phenothiazine, a quantitatively more significant impurity having a tendency to precipitate is retained in solution; and removing any residual impurities still precipitating, despite the addition of water, from the molten material.

* * * * *

UNITED STATES PATENT AND TRADEMARK OFFICE
CERTIFICATE OF CORRECTION

PATENT NO. : 6,664,419 B1
DATED : December 16, 2003
INVENTOR(S) : Bub et al.

It is certified that error appears in the above-identified patent and that said Letters Patent is hereby corrected as shown below:

<u>Title page,</u>
Item [75], Inventor's, should read:
-- [75]   Inventors:     Guenther Bub, Marl (DE)
                                      Juergen Mosler, Castrop-Rauxel (DE) --

Signed and Sealed this

Twenty-third Day of March, 2004

JON W. DUDAS
*Acting Director of the United States Patent and Trademark Office*